_United States Patent_ [19]

Brytus

[11] Patent Number: 5,138,078
[45] Date of Patent: Aug. 11, 1992

[54] GLYCIDYL ESTERS OF TRICARBOXYLIC ACID ADDUCTS

[75] Inventor: Vincent Brytus, Mahopac, N.Y.

[73] Assignee: Ciba-Geigy Corporation, Ardsley, N.Y.

[21] Appl. No.: 625,787

[22] Filed: Dec. 10, 1990

Related U.S. Application Data

[63] Continuation of Ser. No. 494,194, Mar. 15, 1990, abandoned.

[51] Int. Cl.$^5$ ............... C07D 303/08; C07D 303/48; C08G 65/06; C08G 65/02
[52] U.S. Cl. .................. 549/557; 106/287.22; 106/287.21; 528/335; 528/297; 528/361; 528/363; 525/438
[58] Field of Search ............ 106/287.21, 287.22; 549/557; 528/335, 297, 363, 361; 525/438

[56] References Cited

U.S. PATENT DOCUMENTS

| | | | |
|---|---|---|---|
| 3,404,018 | 10/1968 | Hicks | 106/252 |
| 3,631,150 | 12/1971 | Green | 528/361 |
| 3,714,198 | 1/1973 | Metzger et al. | 549/557 |
| 3,790,532 | 2/1974 | Fukutani et al. | 549/557 |
| 4,090,936 | 5/1978 | Barten | 204/159.18 |

_Primary Examiner_—William R. Dixon, Jr.
_Assistant Examiner_—Melissa Bonner
_Attorney, Agent, or Firm_—JoAnn Villamizar

[57] ABSTRACT

A compound of the formula (I)

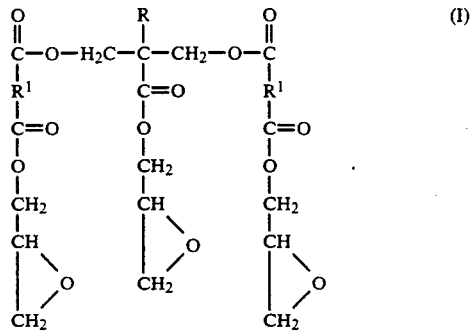

wherein
R is hydrogen, methyl of $C_2$–$C_5$alkyl and $R^1$ is O-phenylene, a saturated or unsaturated 1,2-cyclohexylene group; a 2,3-bicyclo[2.2.2]-hept-5-enyl group of the formula (II)

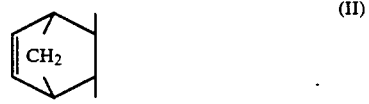

or a saturated or unsaturated aliphatic group of about 2 to about 20 carbon atoms; said O-phenylene is optionally substituted in the ring by one or two alkyl groups of from 1 to 4 carbon atoms; said 1,2-cyclohexylene and bicyclo groups are optionally substituted by one or two alkyl groups of from 1 to 4 carbon atoms and/or by one to six chlorine or bromine atoms; and said aliphatic group is optionally substituted by one or more chlorine or bromine atoms. This compound can be used as a coating compound when mixed with curing agents.

20 Claims, No Drawings

GLYCIDYL ESTERS OF TRICARBOXYLIC ACID ADDUCTS

This application is a continuation of application Ser. No. 494,194, filed Mar. 15, 1990 now abandoned.

BACKGROUND OF THE INVENTION

The formation of adducts of 2,2-dimethylolalkanoic acid with anhydrides provides the intermediates for the production of the glycidyl esters of the present invention. For example, one mole of 2,2-dimethylolpropionic acid (DMPA) with phthalic anhydride yields a tricarboxylic acid adduct as follows:

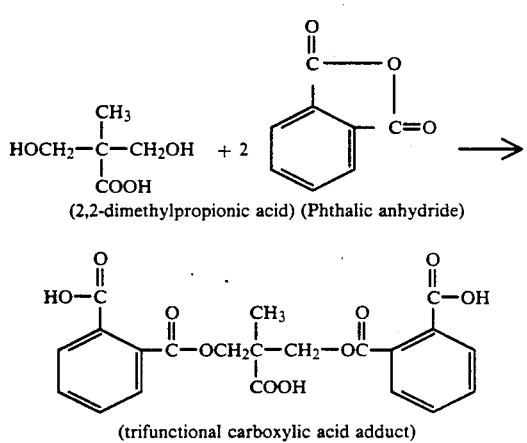

U.S. Pat. No. 3,404,018 describes reaction products of hydroxy-carboxylic acids with liquid epoxy resins (commercial diglycidyl ethers of bisphenol-A). The hydroxy-carboxylic acids used include 2,2-dimethylolpropionic acid as well as adducts formed by reaction of polyols and dicarboxylic anhydrides.

Polyols included in the aforementioned patent are ethylene glycol, propylene glycol, butanediol, polyethylene glycols and glycerine.

Anhydrides included are maleic anhydride, succinic anhydride, dodecenyl succinic anhydride, phthalic anhydride, tetrahydrophthalic anhydride, hexahydrophthalic anhydride, dichloromaleic anhydride, and hexachloro-endomethylene tetrahydrophthalic anhydride.

The polyols are reacted with the anhydrides in a molar ratio of 1:1 under conditions whereby the anhydride ring is opened forming an ester group between one carboxylic acid group of the anhydride and one hydroxy group of the polyol but leaving the remaining carboxylic acid group and the remaining hydroxy groups unesterified.

The reaction of hydroxy mono-acids occurs with the epoxy group of the commercial liquid resin to form a hydroxy-ester with little or no esterification of the carboxyl group with the hydroxyls present in the molecule:

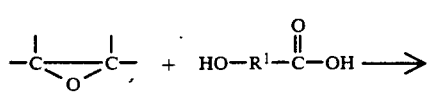

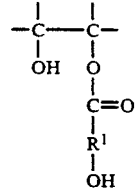

where $R^1$ is an aliphatic, cycloaliphatic or aromatic moiety derived from the monohydroxycarboxylic acid or polyol-anhydride adduct formed by reaction of a polyol and an anhydride.

A primary object of the present invention is to provide novel crosslinking agents for a variety of systems.

A further object of the present invention is to provide compositions useful in coatings and castings that resist the effects of weathering.

SUMMARY OF THE INVENTION

The present invention provides polyglycidyl esters of the general formula (I)

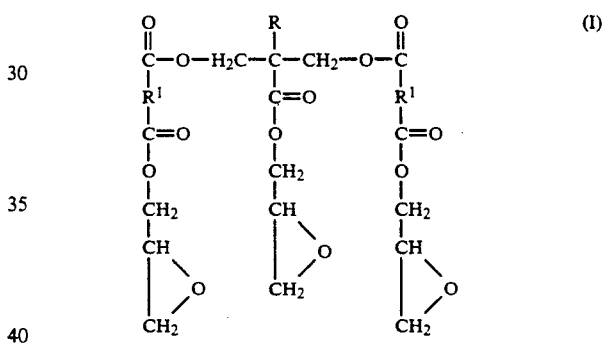

and compositions comprising said polyglycidyl esters.

DETAILED DISCLOSURE

The present invention provides polyglycidyl esters of the general formula (I) using 2,2-dimethylolpropionic acid:

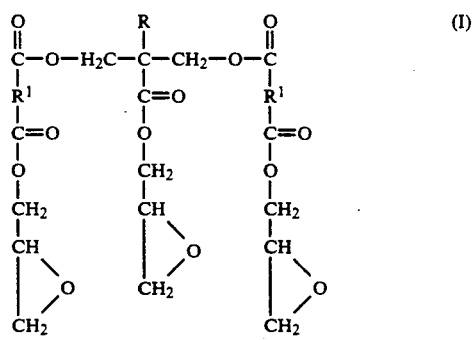

wherein R is hydrogen, methyl or $C_2$–$C_5$ alkyl.

$R^1$ is O-phenylene, a saturated or unsaturated 1,2-cyclohexylene group; a 2,3-bicyclo[2.2.1]-hept-5-enyl group of the formula (II)

(II)

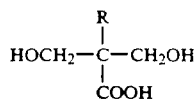
(III)

or a saturated or unsaturated aliphatic group of about 2 to about 20 carbon atoms; said O-phenylene is optionally substituted in the ring by one or two alkyl groups of from 1 to 4 carbon atoms; said 1,2-cyclohexylene and bicyclo groups are optionally substituted by one or two alkyl groups of from 1 to 4 carbon atoms and/or by one to six chlorine or bromine atoms; and said aliphatic group is optionally substituted by one or more chlorine or bromine atoms.

Preferably O-phenylene is unsubstituted or methyl-substituted.

Preferably said 1,2-cyclohexylene group is selected from radicals of the formula

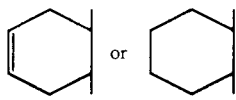

which is unsubstituted or methyl-substituted, preferably in the 3, 4, 5 and 6 positions.

Preferably said bicyclo radical is selected from the group consisting of

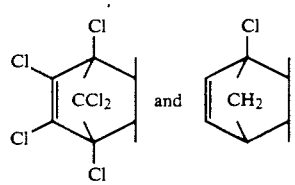

Suitable aliphatic groups are $-CH_2(CH_2)_2CH_2-$, $-CH_2CH_2-$, $-CH_2(CH_2)_{12}CH_2-$ and $-CH=CH-$.

R is preferably hydrogen, methyl or ethyl, most preferably methyl.

The polyglycidyl esters of the present invention can be prepared by glycidylation of tricarboxylic acid adducts of two moles of dicarboxylic anhydride with one mole of 2,2-dimethylolalkanoic acid.

Suitable tricarboxylic acid adducts which can be glycidylated with epichlorohydrin include adducts derived from 2,2-dimethylolalkanoic acids and tetrahydrophthalic anhydride, hexahydrophthalic anhydride, succinic anhydride, maleic anhydride, dodecenyl succinic anhydride, dichloromaleic anhydride, hexachloroendomethylene tetrahydrophthalic anhydride and tetrachlorophthalic anhydride.

Epoxidation of the trifunctional carboxylic adducts formed is accomplished by the use of an excess of epichlorohydrin in the presence of a phase transfer agent, e.g. tetramethyl ammonium chloride followed by dehydrohalogenation with sodium hydroxide utilizing azeotropic removal of water from the reaction to minimize possible saponification of the ester group by the alkaline reagent.

The 2,2-dimethylolalkanoic acids useful in this invention have 4 to 8 carbon atoms and may be represented by the structural formula (III):

wherein R is hydrogen or an alkyl group containing from 1 to 4 carbon atoms. Other specific 2,2-dimethylol alkanoic acids which may be used in this invention are 2,2-dimethylol butyric acid, 2,2-dimethylol valeric acid and 2,2-dimethylol caproic acid.

The preferred 2,2-dimethylol alkanoic acid is 2,2-dimethylolpropionic acid, (2,2-bis-hydroxymethylpropionic acid) hereinafter referred to as DMPA.

Especially preferred is the adduct of DMPA with hexahydrophthalic anhydride to form a tricarboxylic acid adduct of formula (IV):

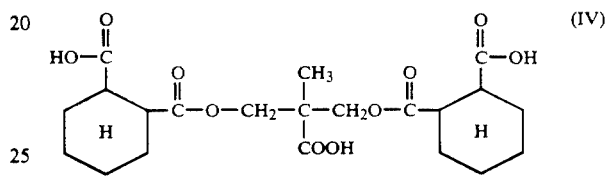
(IV)

The adduct of DMPA with hexahydrophthalic anhydride is a white powder with an acid number of 376 mgm KOH/gm. The polyglycidyl ester of this adduct (formula V) is a clear viscous liquid with an epoxy content of 0.35 to 0.45 eq/100 g.

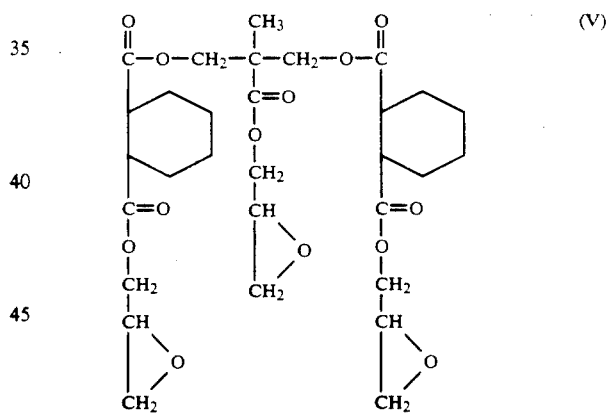
(V)

The instant invention further pertains to a thermosetting coating and casting compositions which comprises
  (a) a polyglycidyl ester of the formula I set forth hereinabove and
  (b) an effective amount of a curing agent which is selected from the group consisting of dicyandiamide, the carboxylic acid functional thermosetting polyesters, the phenolic terminated polyhydroxyethers, the amines, and the anhydrides.

On a weight ratio, when the curing agent is dicyandiamide, for each 85-98 parts of the polyglycidyl ester of component (a), the effective amount of curing agent is 2-15 parts by weight.

On a weight ratio, when the curing agent is a carboxylic acid functional thermosetting polyester, for each 10-30 parts of polyglycidyl ester of component (a), the effective amount of curing agent is 70-90 parts by weight.

On a weight ratio, when curing agent is a phenolic group terminated polyhydroxyether, for each 70–90 parts of polyglycidyl ester of component (a), the effective amount of curing agent is 10–30 parts by weight.

On a weight ratio, when the curing agent is an aliphatic or aromatic amine, such as diaminodiphenylmethane or 4,4'-diaminodiphenyl sulfone, for each 80–90 parts of polyglycidyl ester of component (a), the effective amount of curing agent is 10–20 parts by weight.

On a weight ratio, when the curing agent is an anhydride, such as hexahydrophthalic anhydride, for each 55–65 parts of polyglycidyl ester of component (a), the effective amount of curing agent is 34–45 parts by weight.

The instant coating compositions may also contain solvents, pigments, fillers, flow control agents and other conventional additives normally used in coating compositions involving epoxy resins.

The following examples serve to give specific illustration of the practice of this invention but they are not intended in any way to limit the scope of this invention.

EXAMPLES

Example 1

Preparation of Adduct of DMPA and Hexahydrophthalic Anhydride

A 5.0 liter flask equipped with mechanical stirrer, reflux condenser, nitrogen inlet adapter and thermometer is charged with 1850 g hexahydrophthalic anhydride under nitrogen and the flask is heated to 80° C. Thereafter, 800 g of methyl isobutyl ketone (MIBK) is added followed by 805 g of dimethylolpropionic acid and finally 800 g of MIBK.

The reaction mixture is then heated to 100° C. and held for 5.5 hrs. The flask condenser is then assembled for downward distillation and the MIBK solvent is removed by distilling at 60° C. under reduced pressure (50 mm Hg) and then at 90° C. 1<10 mm Hg.

The residue (product) is discharged in the melt and upon cooling is a white powder. (m.p. 81° C.). An acid number of 376 mgm KOH/g is obtained.

Example 2

Glycidylation of the DMPA/Hexahydrophthalic Anhydride Adduct

A 5 liter flask is equipped with mechanical agitation, a device for separating the epichlorohydrin-water azeotrope and returning the epichlorohydrin to the flask and a thermometer-thermoregulator. A charge of 1100 g of the DMPA-hexahydrophthalic anhydride adduct is made together with 5 g of Irganox 1010 antioxidant (CIBA-GEIGY Corp.) and 49.3 g of 50% aqueous tetramethylammonium chloride (TMAC) solution.

Thereafter, 2509 g of epichlorohydrin is added dropwise to the stirred flask contents at 60° C. and held 30 min. Cooling is applied to maintain the temperature in the 60°–65° C. range.

Thereafter, 49.3 g of 50% aqueous TMAC solution is added and a partial vacuum (ca. 50 mm Hg) is applied to achieve reflux conditions (ca. 65° C.). Then 540 g of 50% aqueous sodium hydroxide solution is added over a period of 4–5 hours to the reaction flask while simultaneously removing water by azeotropic distillation. At the completion of the sodium hydroxide charge, the reamining water is removed over a period of 7 hours and then the vacuum is released and the flask contents allowed to cool to ambient temperature. The batch is then filtered to remove the salt. The filtrate is extracted twice with 750 ml 10% hot aqueous sodium citrate for 5 min. The batch is allowed to separate (10 min) and the upper aqueous layer is removed. The organic layer is filtered.

The final work-up is accomplished as follows:
1. Combine organic layer from several batches.
2. Charge to a 12.0 L 3-neck round bottom flask equipped for vacuum distillation.
3. Charge 262 g 50% aq. NaOH and 105 g 50% aq. TMAC once mixture is warmed to 70° C. Hold solution at 70° C. for 30 minutes.
4. Charge 2000 ml D.I. $H_2O$ and warm batch to 70° C. to redissolve all the precipitate.
5. The organic layer (top layer) is collected and washed with 2000 ml deionized $H_2O$ and 20 g dry ice. The whole mixture is warmed to 70° C. to redissolve any precipitate.
6. The pH value of the water layer (top layer) of the second wash should be below 7.
7. The organic layer (bottom) is collected. Charge 100 g Hyflo super-gel. Distill from 3000 ml MIBK. Filter off super-gel using a pressure filter.
8. Vacuum distill MIBK at 65° C./<10 mm Hg.

The final properties of the product + were as follows:

% yield: 68

% epoxidation: 77

Epoxy content: 0.414 eq/100 g

Acid number: <1

Viscosity @ 25° C.: 16, 800 cP

Chlorine, Total: 1.50%

Chlorine, Hydrolyzable: 1.00%

+2-Methyl, 2-ketoglycidyloxy-1,3-ketoxy bis (β-keto glycidyloxy α-cyclohexyl)propane.

What is claimed is:

1. A compound of the formula (I)

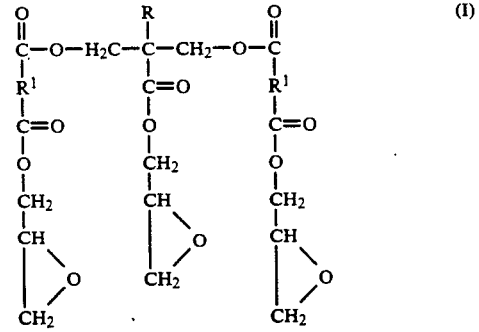

wherein

R is hydrogen, methyl or $C_2$–$C_5$ alkyl and $R^1$ is O-phenylene, a saturated or unsaturated 1,2-cyclohexylene group; a 2,3-bicyclo[2.2.1]-hept-5-enyl group of the formula (II)

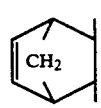

or a saturated or unsaturated aliphatic group of about 2 to about 20 carbon atoms; said O-phenylene is optionally substituted in the ring by one or two alkyl groups of from 1 to 4 carbon atoms; said 1,2-cyclohexylene and bicyclo groups are optionally substituted by one or two alkyl groups of from 1 to 4 carbon atoms and/or by one to six chlorine or bromine atoms; and said aliphatic group is optionally substituted by one or more chlorine or bromine atoms.

2. A compound according to claim 1 wherein R is methyl.

3. A compound according to claim 2 wherein said aliphatic group is about 2 to 12 carbon atoms.

4. A compound according to claim 1 wherein O-phenylene group is unsubstituted or methyl-substituted.

5. A compound according to claim 1 wherein said 1,2-cyclohexylene group is selected from radicals of the formula

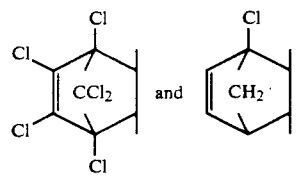

which are unsubstituted or methyl-substituted.

6. A compound according to claim 1 wherein said bicyclo group is selected from the group consisting of

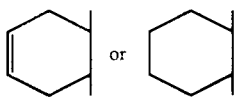

7. A compound according to claim 1 wherein said aliphatic group is $-CH_2(CH_2)_2CH_2-$, $-CH_2CH_2-$, $-CH_2(CH_2)_{12}CH_2-$ or $-CH=CH-$.

8. A compound according to claim 1 of the formula (V)

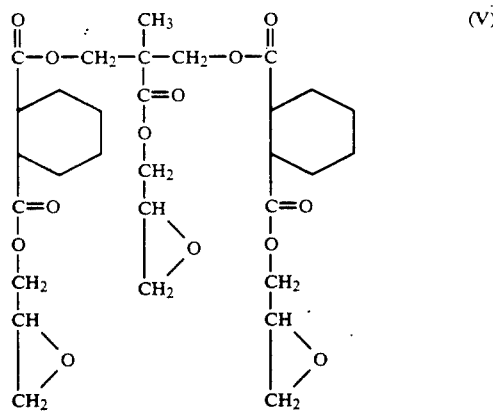

9. A thermosetting coating composition comprising
(a) a polyglycidyl ester of formula (I) according to claim 1 and (b) an effective amount of a curing agent selected from the group consisting of dicyandiamide, carboxylic acid functional thermosetting polyesters, phenolic terminated polyhydroxyethers, amines and the anhydrides.

10. A thermosetting coating composition according to claim 9 wherein said polyglycidyl ester is of the formula (V)

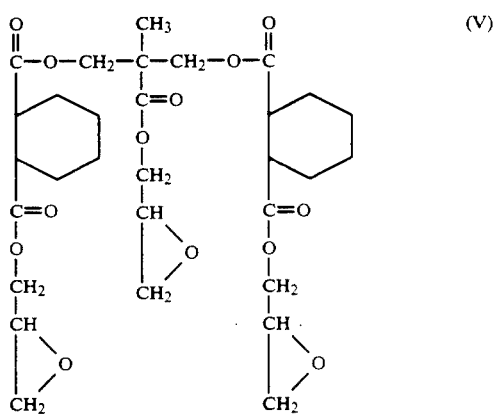

11. A thermosetting coating composition according to claim 9 wherein said curing agent is dicyandiamide.

12. A thermosetting coating composition according to claim 11 wherein for each 85-98 parts of said polyglycidyl ester the effective amount of curing agent is 2-15 parts by weight.

13. A thermosetting coating composition according to claim 9 wherein said curing agent is a carboxylic acid functional thermosetting polyester.

14. A thermosetting coating composition according to claim 13 wherein for each 10-30 parts of polyglycidyl ester the effective amount of curing agent is 70-90 parts by weight.

15. A thermosetting coating composition according to claim 9 wherein said curing agent is a phenolic group terminated polyhydroxyester.

16. A thermosetting coating composition according to claim 15 wherein for each 70-90 parts of polyglycidyl ester the effective amount of phenolic group terminated polyhydroxyester is 10-30 parts by weight.

17. A thermosetting coating composition according to claim 9 wherein said curing agent is an aromatic or aliphatic amine.

18. A thermosetting coating composition according to claim 9 wherein for each 80-90 parts of polyglycidyl ester, the effective amount of amine is 10-20 parts by weight.

19. A thermosetting coating composition according to claim 9 wherein R is methyl in said polyglycidyl ester of formula (I).

20. A thermosetting coating composition according to claim 9 wherein R is 1,2-cyclohexylene in said polyglycidyl ester of formula (I).

* * * * *